United States Patent [19]

Makula et al.

[11] 4,137,222

[45] Jan. 30, 1979

[54] PROTEIN PRODUCT, A PROCESS FOR PREPARATION, AND APPLICATION OF SAID PRODUCT

[75] Inventors: Marie-France Makula; Robert Plan, both of Lyon, France

[73] Assignee: Institut Merieux, France

[21] Appl. No.: 567,403

[22] Filed: Apr. 11, 1975

[30] Foreign Application Priority Data

Apr. 12, 1974 [FR] France ............................. 74 13019

[51] Int. Cl.² ............................................... C07G 7/00
[52] U.S. Cl. .................................. 260/112 B; 424/177
[58] Field of Search ..................................... 260/112 B

[56] References Cited

U.S. PATENT DOCUMENTS

| | | | |
|---|---|---|---|
| 2,793,203 | 5/1957 | Schultze | 260/112 B |
| 2,922,745 | 1/1960 | Singher | 260/112 B |
| 3,382,227 | 5/1968 | West | 260/112 B |
| 3,415,804 | 12/1968 | Polson | 260/112 B |
| 3,763,135 | 10/1973 | Shanbrom | 260/112 B |
| 3,808,124 | 4/1974 | Dziobkrowski | 260/112 B |
| 3,943,245 | 3/1976 | Silverstein | 260/112 B |

OTHER PUBLICATIONS

H. L. Taylor, J. Am. Chem. Soc., vol. 78, p. 1356–1358, 1956.
Chemical Abstracts, vol. 48, No. 13781c, Horejsi, 1954.
Chem. Abs., vol. 54, No. 2470i, Saifer, 1960.
Chem. Abs., vol. 49, No. 5567a, Horejsi, 1954.
Chem. Abs., vol. 50, No. 15616b, Horejsi, 1956.
Chem. Abs., vol. 56, No. 15793e, Stastny, 1961.
Chem. Abs., vol. 55, No. 21485d, Gubenko, 1961.

*Primary Examiner*—Paul R. Michl
*Attorney, Agent, or Firm*—Cushman, Darby & Cushman

[57] ABSTRACT

A gamma globulin-rich fraction from conventional ethanol fractionation of whole placenta is treated (i) with 17% ethanol at pH 5.1 (itself a conventional step in the fractionation)
(ii) the precipitate is diluted with water and dialysed to remove alcohol, then LEDA (2-ethoxy-6, 9-diaminoacridine lactate) is added and the precipitate preferably at pH 7.7 ± 0.5 discarded
(iii) ammonium sulphate at approximately semi-saturation is added and the precipitate collected.

This precipitate contains a proteolytic enzyme (plasmin), assayed by caseinolysis and useful for removal of anti-complement from gamma globulin preparations.

7 Claims, No Drawings

PROTEIN PRODUCT, A PROCESS FOR PREPARATION, AND APPLICATION OF SAID PRODUCT

The present invention has for its object a new protein product prepared from human blood contained in the placenta. This product is rich in gamma-globulins which can be used directly by the venous route or together with standard gamma-globulins to which it gives clinical tolerance by the intravenous route. It is thus possible to obtain an intravenous gamma-globulin from placentas under advantageous economic conditions without involving the bleeding of human beings.

It is known that gamma-globulins have an antibody activity which permit them to be used therapeutically, for example in the treatment or prevention of infections having a microbial or viral origin, particularly in the case of patients suffering from immunitary deficiencies.

Gamma-globulins are prepared from serum or blood extracted from placentas. The most frequently used process is a fractionation process by means of alcohol.

The gamma-globulin preparation process from placentas was described by H. L. Taylor, J. Am. Chem. Soc., vol. 78, 1356, 1956.

This process consists of treating a filtrate of a saline suspension of pulverised placenta in such a way as to obtain an ethanol concentration equal to 25% by volume. Precipitate I is collected and treated by means of 8% ethanol at pH 4.8. The precipitate is eliminated and the supernatant product II is collected. By adding alcohol to this supernatant product until a concentration of 25% by volume is obtained, a fraction III which is rich in gamma-globulins is precipitated. Precipitate III is treated by means of 17% ethanol at pH 5.1. Precipitate III-1 is eliminated and the supernatant product III-1 is collected. By adding ethanol to the supernatant product until a concentration of 25% by volume is obtained a precipitate of III-2 of gamma-globulins is obtained which are identical to those obtained by fractionation of the blood plasma.

It is known that gamma-globulin preparations obtained by ethanol fractionation (called hereinafter standard gamma-globulins) are well tolerated when administered by the intramuscular route. However, often serious reactions have been observed when the intravenous route is used.

This poor tolerance has been attributed to anti-complementary activity due to the presence of aggregates which can fix the complement, as happens with the antigen-antibody complex.

This complement fixation corresponds to an activation of several enzymes whose products are responsible for intolerance reactions recorded after the intravenous injection of standard gamma-globulins.

Various processes are known making it possible to obtain gamma-globulins which can be intravenously injected. These processes consist of subjecting standard gamma-globulin either to incubation at pH 4 or to an enzymatic digestion by pepsin, papain or plasmin.

In the Taylor process mentioned hereinbefore precipitate III-1 was eliminated.

It has now been found that by subjecting precipitate III-1 to an appropriate treatment it is possible to recover a gamma-globulin fraction which is rich in plasmin which was lost in the Taylor process, and thus obtain a protein product which can be used either as it is or for eliminating or reducing the anti-complementary activity of standard gamma-globulin while bringing about a concentration of gamma-globulins in the thus treated standard preparation.

The object of the present invention is a novel industrial product comprising a protein product obtained in the following manner:

The starting product is the precipitate III-1 obtained during the conventional ethanol fractionation process of placental blood mentioned hereinbefore. Precipitate III-1 is diluted with water, the residual alcohol is eliminated by dialysis, an aqueous solution of 2-ethoxy-6,9-diamino-acridine lactate (L.E.D.A.) is added to the solution obtained, the precipitate formed is eliminated at pH 7.7 ± 0.5 and preferably between 7.5 and 8.0, to the filtrate is added an aqueous solution of ammonium sulphate at a concentration corresponding approximately to semi-saturation and the precipitate formed is isolated, this being the protein product forming the object of the invention.

This protein product contains a proteolytic enzyme (plasmin) whose content is defined by means of a caseinolytic unit.

The caseinolytic unit is defined as the quantity of plasmin producing a 450 $\mu$g increase of tyrosine soluble in trichloro-acetic acid on 3% casein for 1 hour at 37° C., cf. "The preparation of human fibrinolysin", Scouris et. al, Vox Sanguinis 1960, vol. 5, no. 4, pp. 357–376.

Generally the protein product according to the invention contains 10 to 100 caseinolytic units per gram of protein, but this content can be below 10 units.

The invention also has for its object a process for the preparation of the said protein product.

According to a preferred embodiment, the treatment by means of 2-ethoxy-6,9-diamino-acridine lactate is performed at an alkaline pH value. For this purpose a base is added to the protein solution before adding 2-ethoxy-6,9-diamino-acridine lactate. This base is, for example, an alkaline metal hydroxide such as soda. The 2-ethoxy-6,9-diamino-acridine lactate is added in such a quantity as to obtain a concentration thereof such that the weight thereof represents one-twentieth to one-quarter of the weight of proteins present in the solution. The protein content of the solution to be treated is generally between 5 and 30 g/liter and preferably of the order of 20 g/liter. Taking as an example a content of 20 g/liter, the 2-ethoxy-6,9-diamino-acridine lactate should be added in a quantity sufficient to obtain a final concentration thereof between about 0.1 and 0.5%.

The precipitate obtained after adding 2-ethoxy-6,9-diamino-acridine lactate is eliminated by centrifuging. An aqueous semi-saturated ammonium sulphate solution, i.e., a solution containing about 300 g of ammonium sulphate per liter is then added to the filtrate. The precipitate of the protein product formed is isolated by filtration. This protein product can be purified if desired by placing in an aqueous solution and dialyzing.

According to a preferred embodiment, prior to the 2-ethoxy-6,9-diamino-acridine lactate treatment stage a preliminary stage is performed consisting of eliminating the insoluble fraction at pH 4.8 ± 0.2, and more particularly at a pH of 4.8 to 5.0. To this end an acid such as hydrochloric acid is added to the solution of precipitate III-1. The precipitate formed is then eliminated, for example by centrifuging. This non-obligatory preliminary stage facilitates the following 2-ethoxy-6,9-diamino-acridine lactate treatment stage and has the effect of eliminating lipo proteins present in the solution.

All the stages of the process defined hereinbefore can be performed at a temperature between about 0° and 25° C.

The invention also has for its object the application of the said protein product to the obtention of gamma-globulins which can be used by the intravenous route either directly or by treating a standard gamma-globulin by means of the said protein product.

According to the said application an aqueous solution of the said protein product, optionally mixed with an aqueous solution of standard gamma-globulins is incubated until the anti-complementary power has disappeared. It is conventionally considered that the anti-complementary power disappears when the 50 mg/ml solution does not neutralize, i.e., fix 2 50% complement units (2 by 50% C' units). In other words, it is considered that the anti-complementary power disappears when a concentration in excess of 50 mg/ml is necessary for fixing 2 50% complement units (Public Health Monograph No. 74 1965, U.S.A.: Standardised Diagnostic Complement Fixation Method and Adaptation to Microtest).

According to a preferred embodiment, this application has the characteristics indicated hereinafter.

The solution which is subjected to incubation can for example contain 50–160 g/liter of proteins. The titre of caseinolytic units in the solution which undergoes incubation is between about 0.25 and 10 caseinolytic units per gram of proteins, and more particularly 4 to 6 caseinolytic units per gram of proteins.

Incubation is performed at a pH between about 4 and 7. The incubation temperature is between about 10° and 45° C., preferably it is 37° C. The incubation reaction time depends on the pH, the temperature, the titre in caseinolytic units of the starting mixture and the maximum titre of the final anti-complementary power selected.

The incubation period decreases when the pH decreases and when the temperature increases.

When the incubation is carried out at 37° C. and a pH of 7, generally 14 to 29 days are necessary for the anti-complementary power titre to be satisfactory.

When working at 37° C. and pH 4 an incubation period of 18 hours suffices, or more reliably 24 to 48 hours.

After incubation the gamma-globulin solution is preferably subjected to the adsorbing action of bentonite in order to eliminate the residual proteolytic enzyme. Thus, for example a 4% bentonite suspension sterilized in the autoclave is added in such a way as to add about 5 grams of bentonite per 100 grams of proteins in the solution. The pH is adjusted between 4 and 8, for example about 5.5 and stirring takes place for a few hours at a temperature between about 20° and 37° C., for example 2 hours at ambient temperature (20° to 25° C.). Finally, the bentonite is removed, for example by centrifuging.

However, when the titre of the caseinolytic units is low, for example less than 2 caseinolytic units per gram of proteins, the bentonite treatment can be omitted.

When the solution obtained after incubation is pyrogenic or colored it is advantageous to subject it, for example, to the adsorbing action of an alumina gel (gel obtained by the Willstätter process in an aqueous medium). To this end a quantity of alumina gel between about 0.25 and 1 times the protein weight in the solution is added. This treatment is performed at pH 5.5 ± 0.5 and a temperature between 20° and 45° C., these values being approximate. Stirring takes place for a few hours, for example 3 hours at 45° C. The alumina is then removed by centrifuging.

The thus obtained gamma-globulin differs from standard gamma-globulin more particularly as a result of the ultra-centrifuging and filtration gel characteristics as well as by the absence of an anti-complementary power (the absence of an anti-complementary power being conventionally defined with the aid of the maximum threshold indicated hereinbefore). Clinical tests have shown that the gamma-globulin obtained by the process of the invention can be administered intravenously even to patients who cannot take standard gamma-globulin by the venous route.

To preserve the gamma-globulin obtained after incubation and optionally after bentonite or alumina treatment, it is subjected to a lyophilization process. Thus a gamma-globulin product is obtained which can be used intravenously after aqueous re-dissolving.

It has also been found and this is also an object of the invention that after lyophilization a powder is obtained whose solubility and stability are improved when lyophilization is performed in the presence of glycocoll in a proportion of 1 g of glycocoll for 2 to 3 g of proteins, and preferably 1 g of glycocoll for 2.5 g of proteins. The following Examples serve to illustrate the invention.

EXAMPLE 1

Precipitate III-1 obtained according to the Taylor process is dissolved in 1½ times its weight of aqueous sodium chloride solution at a rate of 8 grams per liter cooled to 0° C. The solution is subjected to dialysis under running water at +4° C. for 3 to 4 days, then the dialyzed liquid is diluted with water (10 times the weight of the initial precipitate). If necessary, the pH is adjusted to 4.8 by adding a normal hydrochloric acid solution. The diluted liquid is centrifuged and the precipitate formed eliminated.

The pH of the supernatant liquid is adjusted to 7.7 by adding a normal soda solution followed by the addition of sodium chloride at a rate of 2 g per 1000. 2-ethoxy-6,9-diamino-acridine lactate (in the form of a 1% solution) is added. To obtain a good precipitation, i.e., an at least 50% sediment and a perfectly clear supernatant product, it is generally necessary to add the 2-ethoxy-6,9-diamino-acridine lactate in such a way as to obtain a concentration of 1 to 5 grams per 1000. The optimum quantity thereof can easily be determined on samples to which are added progressively increasing quantities of 2-ethoxy-6,9-diamino-acridine lactate. Sedimentation takes place for at least 2 hours followed by the elimination by centrifuging of the precipitate and the addition of sodium chloride to the supernatant product in order to crystallize the excess 2-ethoxy-6,9-diamino-acridine lactate. The precipitate formed is then filtered off.

Ammonium sulphate is added to the filtrate in a quantity of 300 grams per liter of filtrate. Stirring takes place to completely dissolve the ammonium sulphate and the pH which must be between about 6 and 7 is checked. The precipitate formed is collected by filtering followed by dialysis.

Glycocoll is added to obtain a 1% concentration and the pH is adjusted to 7 followed by sterile filtration.

Thus, a solution to be designated hereinafter by A is obtained.

The anti-complementary power of solution A is titrated, followed by the optional incubation at 37° C.

until the anti-complementary power is satisfactory, i.e., in excess of 50 mg/ml fixing 2 50% C' units.

When this result is obtained incubation is discontinued. The proteins are dosed and the titre of caseinolytic units determined. If the latter exceeds 0.2 units per milliliter for a solution of 100 grams of proteins per liter, bentonite treatment is carried out. For this purpose a 4% solution of autoclaved bentonite is added in a sufficient quantity to provide 5 grams of bentonite per 100 grams of protein. The pH is adjusted to 5.5 by adding a normal hydrochloric acid solution followed by stirring for 2 hours at ambient temperature. The bentonite is removed by centrifuging. If the titre in caseinolytic units is still above the threshold indicated hereinbefore, the bentonite treatment must be repeated.

Alumina gel treatment is performed. As a function of the pyrogens and color an alumina gel weight between 1 and 0.25 times the weight of proteins present is added. In the present example half the weight of the proteins present is added. The pH is adjusted to 5.5 followed by stirring for 3 hours at 45° C. The alumina gel is then removed by centrifuging.

Protein dosing is carried out, the pH is adjusted to 7 by adding a normal soda solution and distilled water is added to adjust the titre of the proteins to 52 grams per liter. Sodium chloride is added to obtain a concentration of 1 gram per liter and glycocoll to obtain a concentration of 20 grams per liter. This is followed by sterile filtration.

The solution obtained is subjected to lyophilization whereby a gamma-globulin product was obtained which can be used intravenously after sterile aqueous re-dissolving.

EXAMPLE 2

Prior to incubation, solution A obtained in Example 1 is added to a standard gamma-globulin solution in such a way as to adjust the titre to 5 caseinolytic units per gram of proteins.

If for example it is desired to treat 10 liters of standard gamma-globulin containing 154 grams of proteins per liter, it is necessary to add x liters of a solution A such as obtained in Example 1 containing 125 grams of protein per liter and titrating 2000 caseinolytic units per liter.

x is easily determined in the following manner:

$$\frac{x \times 2000 \text{ cu/l } 5}{125 x + 154 \times 10 \text{ l}}$$

i.e. $x = \frac{7700}{1375}$ or about 5.6 liters

After checking the sterility the mixture is incubated at 37° C. and pH 7. The anti-complementary power is checked regularly, for example every 8 days and an analysis sample until it disappears. This generally takes 14 to 28 days. The anti-complementary power is considered to have disappeared when it is greater than 50 mg/ml fixing 2 50% C' units. Incubation is stopped and treatment with bentonite and alumina gel is carried out under the same conditions as in Example 1.

EXAMPLE 3

Working takes place in an analogous manner to that described with reference to Example 2, but solutions A such as obtained in Example 1 is added under different pH and enzymatic concentration conditions.

The enzymatic concentration is adjusted to 1.25 caseinolytic units per gram of proteins. Incubation is carried out at pH 4 for 18 hours at 37° C. Working then takes place as described in Example 1 but bentonite treatment is omitted.

A gamma-globulin product is obtained which can be used intravenously after aqueous dissolving.

What we claim is:

1. A process for preparing a protein product which is rich in gamma globulins and which also contains plasmin consisting essentially of diluting with water a Taylor precipitate III-1 fraction, treating the resulting solution with a 2-ethoxy-6,9-diamino acridine lactate solution whereby a precipitate is formed, eliminating the thus formed precipitate, adding to the resulting filtrate an aqueous semi-saturated ammonium sulphate solution whereby a precipitate is formed and isolating the thus formed precipitate containing said protein product which is rich in gamma globulins and which also contains plasmin.

2. The process of claim 1 wherein treating said water solution of the Taylor precipitate III-1 fraction with said 2-ethoxy-6,9-diamino acridine lactate solution is carried out at an alkaline pH of about 7.7 ± 0.5.

3. The process of claim 1 wherein 2-ethoxy-6,9-diamino acridine lactate is added in an amount so as to obtain a concentration thereof between about 0.1 and 0.5%.

4. The process of claim 1 wherein said precipitate containing said protein product which is rich in gamma globulins and which also contains plasmin is isolated by centrifugation.

5. The process of claim 1 which also includes placing said precipitate containing said protein product which is rich in gamma globulins and which also contains plasmin in water and dialyzing the same.

6. The process of claim 1 which also includes, prior to treating the resulting solution of water and Taylor precipitate III-1 fraction with a 2-ethoxy-6,9-diamino lactate acridine solution, the step of eliminating a fraction insoluble at pH 4.8 ± 0.2.

7. A process for preparing a protein product from human blood contained in the placenta consisting essentially of treating a filtrate of a saline suspension of pulverized placenta to obtain an ethanol concentration of 25 volume percent whereby a first precipitate is formed, collecting said first precipitate and treating the collected first precipitate with 8 percent ethanol at pH 4.8 whereby a second precipitate and a first supernatant product are formed, eliminating said second precipitate and collecting said first supernatant product, adding ethanol to said first supernatant product to obtain an ethanol concentration of 25 volume percent whereby a third precipitate is formed, collecting said third precipitate and treating the collected third precipitate with 17% ethanol at pH 5.1 whereby a fourth precipitate is formed, collecting said fourth precipitate and diluting the same with water, treating the resulting solution with a 2-ethoxy-6,9-diamino acridine lactate solution whereby a fifth precipitate is formed, eliminating the thus formed fifth precipitate, adding to the resulting filtrate an aqueous semi-saturated ammonium sulphate solution whereby a sixth precipitate is formed and isolating the thus formed sixth precipitate containing said protein product which is rich in gamma globulins and which also contains plasmin.

* * * * *

UNITED STATES PATENT AND TRADEMARK OFFICE
CERTIFICATE OF CORRECTION

PATENT NO. : 4,137,222
DATED : January 30, 1979
INVENTOR(S) : Marie-France Makula and Robert Plan It is certified that error appears in the above—identified patent and that said Letters Patent are hereby corrected as shown below:

Col. 5 - The equation at lines 47-48 should read $$-- \frac{\tau \times 2000 \text{ cu}/\ell}{125\tau + 154 \times 10} = \frac{5}{1} --$$

Signed and Sealed this

Twentieth Day of November 1979

[SEAL]

Attest:

RUTH C. MASON
*Attesting Officer*

LUTRELLE F. PARKER
*Acting Commissioner of Patents and Trademarks*